United States Patent
Murphy et al.

(10) Patent No.: US 11,622,696 B2
(45) Date of Patent: *Apr. 11, 2023

(54) METHOD FOR IMPROVING HEART RATE ESTIMATES BY COMBINING MULTIPLE MEASUREMENT MODALITIES

(71) Applicant: Verily Life Sciences LLC

(72) Inventors: Mark Murphy, Palo Alto, CA (US); Russell Norman Mirov, Los Altos, CA (US); Christopher Towles Lengerich, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/032,074

(22) Filed: Sep. 25, 2020

(65) Prior Publication Data
US 2021/0015379 A1 Jan. 21, 2021

Related U.S. Application Data

(63) Continuation of application No. 15/346,144, filed on Nov. 8, 2016, now Pat. No. 10,786,164.

(60) Provisional application No. 62/266,593, filed on Dec. 12, 2015.

(51) Int. Cl.
*A61B 5/024* (2006.01)
*A61B 5/0245* (2006.01)
*A61B 5/00* (2006.01)
*G04G 21/02* (2010.01)

(52) U.S. Cl.
CPC ........ *A61B 5/02438* (2013.01); *A61B 5/0245* (2013.01); *A61B 5/02416* (2013.01); *A61B 5/681* (2013.01); *A61B 5/721* (2013.01); *A61B 5/7221* (2013.01); *A61B 5/7275* (2013.01); *A61B 5/742* (2013.01); *G04G 21/025* (2013.01)

(58) Field of Classification Search
None
See application file for complete search history.

(56) References Cited

U.S. PATENT DOCUMENTS 10,786,164 B2 * 9/2020 Murphy ............. A61B 5/02438

\* cited by examiner

*Primary Examiner* — Meredith Weare
(74) *Attorney, Agent, or Firm* — McDonnell Boehnen Hulbert & Berghoff LLP

(57) ABSTRACT

Systems and methods are provided for determining the frequency of a cardiovascular pulse based on a first physiological signal that is continuously available and a second physiological signal that is less available and that is more accurate or otherwise improved relative to the first signal with respect to pulse rate estimation. When the second signal is available it controls the determination of the pulse rate. When the second signal is unavailable, the first signal is used to determine the pulse rate. This can include using the first signal to estimate the pulse rate until the second signal is available, at which point the pulse rate is estimated based on the second physiological signal. Alternatively, the first signal could be used to determine a number of candidate pulse rates, and the second signal could be used to select a pulse rate from the set of candidate pulse rates.

20 Claims, 6 Drawing Sheets

METHOD FOR IMPROVING HEART RATE ESTIMATES BY COMBINING MULTIPLE MEASUREMENT MODALITIES

CROSS-REFERENCE TO RELATED APPLICATIONS

This application is a continuation of U.S. application Ser. No. 15/346,144, filed Nov. 8, 2016, which claims the benefit of U.S. Provisional Application No. 62/266,593, filed Dec. 12, 2015. The foregoing applications are incorporated herein by reference.

BACKGROUND

Unless otherwise indicated herein, the materials described in this section are not prior art to the claims in this application and are not admitted to be prior art by inclusion in this section.

A variety of cardiovascular parameters can be detected by illuminating blood in a portion of subsurface vasculature and detecting one or more properties of light responsively emitted from the portion of subsurface vasculature (e.g., reflected, fluorescently re-emitted, scattered, or otherwise emitted from. Such cardiovascular parameters can include a volume of blood over time, a pulse rate of blood, a flow rate of blood over time, a blood pressure, an oxygen saturation, a timing of pulses of blood, or some other properties of blood in the portion of subsurface vasculature at one or more points in time. Cardiovascular parameters may additionally or alternatively be detected by detecting a biopotential between two or more locations of a body, by detecting sounds generated by the body (e.g., by the heart, lungs, and/or blood), by emitting ultrasound into the body and detecting ultrasound that is responsively emitted from the body, or by some other means. Such cardiovascular parameters can be detected over a protracted period of time, e.g., using a body-mountable device, to determine a health state of a person.

SUMMARY

Some embodiments of the present disclosure provide a method including: (i) detecting, via a first sensor, a first signal related to a cardiovascular pulse; (ii) sampling the first signal during a first period of time to obtain a first set of samples of the first signal; (iii) determining that a second signal related to the cardiovascular pulse is being detected, during the first period of time, via a second sensor; (iv) responsive to determining that the second signal related to the cardiovascular pulse is being detected during the first period of time via the second sensor: (1) determining a second-signal pulse rate based on the second signal; (2) determining a pulse rate for the first period of time based on (a) the first set of samples of the first signal and (b) the second-signal pulse rate; and (3) providing, via a user interface, an indication of the pulse rate for the first period of time; (v) sampling the first signal during a second period of time to obtain a second set of samples of the first signal; (vi) determining a pulse rate for the second period of time based on the second set of samples of the first signal; and (vii) providing, via the user interface, an indication of the pulse rate for the second period of time.

Some embodiments of the present disclosure provide a system including: (i) a first sensor; (ii) a second sensor; (iii) a user interface; and (iv) a controller that is operably coupled to the first sensor and the second sensor and that includes a computing device programmed to perform controller operations. The controller operations include: (1) operating the first sensor to detect a first signal that is related to a cardiovascular pulse; (2) sampling the first signal to obtain a set of samples of the first signal; (3) operating the second sensor to detect a second signal; (4) determining whether the detected second signal is related to the cardiovascular pulse and, if it is determined that the detected second signal is related to the cardiovascular pulse, determining a second-signal pulse rate; (5) determining a first pulse rate based on (a) the set of samples of the first signal and, if it is determined that the detected second signal is related to the cardiovascular pulse, (b) the second-signal pulse rate; and (6) providing, via the user interface, an indication of the first pulse rate.

These as well as other aspects, advantages, and alternatives, will become apparent to those of ordinary skill in the art by reading the following detailed description, with reference where appropriate to the accompanying drawings.

DETAILED DESCRIPTION

Figure 1A:
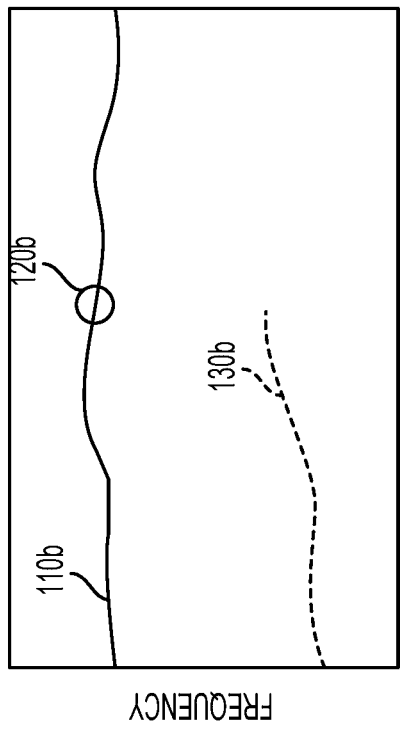
FIG. 1A is an example of predicted pulse rates over time.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where detection of the frequency and/or rate of oscillating patterns in biosignals (e.g., determining a breathing rate, determining a gait cycle frequency) or other signals of interest is desired. The signals of interest could be detected from any living or non-living body or a portion thereof or from some other environment and/or variable or parameter of interest.

I. OVERVIEW

In a variety of applications the frequency of an oscillating pattern in a detected signal can be related to a property of interest. For example, a volume of blood in a portion of subsurface vasculature, a pattern of electrical potential across a body, a pressure or displacement of a blood vessel or surrounding tissue, or some other signals could include an oscillating pattern related to a cardiovascular pulse (e.g., a rate of pulses of blood in the portion of subsurface vasculature, a rate of occurrence of electrical events related to activity of a heart). Such signals could be detected by multiple sensors and the outputs of such sensor could be used, in combination, to determine a frequency of interest (e.g., a pulse rate of the cardiovascular pulse). Other properties could be related to the frequency of oscillating patterns in other detected signals Different signals (detected, e.g., by respective different sensors) that are related to a cardiovascular pulse (or other repeating process of interest) could have respective different noise characteristics, noise spectra, systematic errors, or other properties and the combination of the different signals to determine a pulse rate (or other frequency or rate metric) could be performed in view of such differences. For instance, a first signal could be used to generate pulse rate estimates having a high accuracy but a low resolution while a second signal could be used to generate multiple high-sensitivity, high-resolution estimates of the pulse rate but with uncertainty regarding which of the estimates is the correct estimate. In such an example, the first and second signals could be combined to determine a pulse rate by using the first signal pulse rate estimate to select one of the second signal pulse rate estimates.

In some examples, the different signals could differ with respect to the timing of availability of the signal for determining a pulse rate, e.g., a first signal could be consistently available and relatively low-quality (e.g., able to be used to generate relatively low-resolution, low-accuracy, or otherwise low-quality estimates of a pulse rate, or multiple high-sensitivity, high-resolution estimates with uncertainty regarding which estimate is correct) while a second signal could be relatively high-quality but only occasionally usable. For example, the first signal could be detected by a sensor that is in consistent contact with a body (e.g., a photoplethysmographic sensor mounted to a wrist by a watch or other wrist-mounted device) and the second signal could be a sensor that is in inconsistent contact with the body due to relative motion between the body, the availability of the second signal being conditional on a user performing some action (e.g., contacting a sensor with fingers of one or both hands of the user), or due to some other factor or process.

In such examples, the second signal could be used, when available, to determine the pulse rate (possibly in combination with the first signal); when the second signal is not available, the first signal could be used to determine the pulse rate. This could include using the second signal to determine a pulse rate for a first period of time when the second signal is available (e.g., using pulse rates determined using the second signal as 'ground truth' values of the pulse rate of a cardiovascular pulse for those periods of time when the second signal is available). For periods of time when the second signal is not available for determining pulse rates, the first signal could be used to determine the pulse rate in combination with the pulse rate determined for the first period of time using the second signal. This could include updating the determined pulse rate using samples of the first signal that are received after the first period of time, e.g., using an inertial filter, a Kalman filter, the Viterbi algorithm, or some other method with the pulse rate determined for the first period of time based on the second signal serving as a starting value or constraint. In some examples, pulse rates could be determined retrospectively, for points in time before the first period of time, based on the determined pulse rate and using samples of the first signal received before the first period of time.

Using an occasionally available signal (e.g., the 'second signal' above) to determine a pulse rate could include determining whether the signal can be used to reliably determine a pulse rate. This could include determining a noise magnitude, determining a signal-to-noise ratio, performing pattern matching to detect QRS complexes or other characteristic features of the signal and/or to determine a level of distortion of such features, or performing some other determination based on the detected signal. Additionally or alternatively, some further signal could be detected to determine whether the occasionally available signal is available to determine a pulse rate, e.g., an electrode impedance signal to determine whether electrodes of a sensor are in electrical contact with a target, a force or pressure sensor to determine whether a sensor is in secure contact with a body surface, or an accelerometer to determine whether a sensor has a stable location (e.g., relative to a body surface). If it is determined that a pulse rate can be determined from the occasionally available signal (e.g., that a QRS complex can be consistently extracted from the signal, and a pulse rate determined from such extracted QRS complexes), a pulse rate could be determined as described above.

In some examples, sensors configured to detect such signals as are described above could be included in one or more body-mountable devices. For example, a first sensor could be a photoplethysmographic sensor configured to detect an optical signal related to the volume of blood in a portion of subsurface vasculature and could be included in a wrist-mounted device. This first sensor could provide a signal that is related to a cardiovascular pulse and that is substantially continuously available to, e.g., determine a pulse rate of the cardiovascular pulse. A second sensor could be an accelerometer configured to detect motion (e.g., displacement of the skin that is related to the cardiovascular pulse when the second sensor is in stable mechanical contact with the skin), a potential difference (e.g., an electrocardiographic potential difference between electrodes that is related to the cardiovascular pulse when the electrodes are in stable electrical contact with respective locations on the skin), or some other signal that is occasionally related to the cardiovascular pulse. This second sensor could provide a signal that can occasionally be used to determine a pulse rate of the cardiovascular pulse. The second sensor could be included in a necklace, a garment, a blanket, or some other body-mountable device. The devices that include the first and second sensors could be in communication with each other and/or with some other system such that the signals from the first and second sensors can be used to determine pulse rates for the cardiovascular pulse over time. Alternatively, such first and second sensors could be included in the same body-mountable device.

The methods described herein to determine a pulse rate of a cardiovascular pulse based on multiple different signals that are available during respective different periods of time (e.g., a first signal that is substantially continuously available to determine a pulse rate and a second signal that is only occasionally available to determine a pulse rate) could be applied to a variety of signals detected by a variety of means to determine the frequency or other rate information for a variety of different environments or physical processes. It should be understood that the above embodiments, and other embodiments described herein, are provided for explanatory purposes, and are not intended to be limiting.

II. DETERMINATION OF PULSE RATES FROM MULTIPLE DETECTED PHYSIOLOGICAL SIGNALS

A variety of signals or variables can include oscillating signals and/or other repeating patterns or events having a frequency or rate that can be determined and that is related to a property of interest. In a particular example, a pulse rate of a cardiovascular pulse could be determined based on one or more detected physical variables that are related, at least occasionally, to the cardiovascular pulse, e.g., an electric current or potential in a body (e.g., an electrocardiogram (ECG)), a volume, flow rate, pressure, or other properties of blood in a portion of vasculature (e.g., a volume of blood in a portion of subsurface vasculature in a wrist of a body), a displacement or motion over time of tissue (e.g., skin over a portion of subsurface vasculature), or some other physical variable. Multiple such physical variables could be detected and used, in combination, to determine the pulse rate.

A single wearable device, e.g., a wrist-mountable device, could include one or more sensors configured to detect such multiple physical variables (e.g., a first sensor to illuminate a portion of subsurface vasculature and detect a volume of blood in the portion of subsurface vasculature based on a detected intensity of responsively emitted light, and a second sensor that includes electrodes to detect an electrocardiographic potential when a user contacts the electrodes with skin of opposite arms of the user). Alternatively, multiple devices (e.g., multiple wearable or otherwise body-mountable devices) could include respective sensors and the outputs of such sensors could be used to determine a pulse rate. A pulse rate of a cardiovascular pulse (or a rate or period of some other repeating event or process), could then be determined, using methods described herein, based on such multiple detected signals.

In some examples, first and second signals, detected by respective first and second sensors, could have respective different noise characteristics, periods of availability to determine a pulse rate (e.g., due to time-varying noise characteristics and/or intermittent access of a sensor to a corresponding tissue or other object of interest), or other characteristics that differ between the signals, and the first and second signals could be used, in view of such differences, to determine a pulse rate. In some examples, a first signal could be substantially continuously available for use in determining a pulse rate, e.g., due to being detected by a sensor that is securely mounted to an external skin surface proximate a portion of subsurface vasculature or securely mounted to some other physical system of interest from which the first signal is detected. A second signal could be intermittently available for use in determining the pulse rate, e.g., due to the sensor being loosely associated with a body or otherwise in inconsistent contact with a target tissue or due to some other process resulting in a time-varying amount of noise in the second signal. The second signal, when available, could be used to improve the determination of pulse rates, e.g., by determining an average pulse rate from pulse rates determined for each of the signals, by combining the first and second signals (e.g., via a linear combination) and determining a pulse rate from the combined signal, or according to some other method.

In some examples, the second signal could, when available to determine a pulse rate, be used to provide a higher-quality pulse rate estimate than a pulse rate determined using the first signal. For example, the first signal could include harmonics, motion artifacts, or other contents that result in an ambiguous determination of the pulse rate (e.g., the determination of multiple pulse rates corresponding to multiple harmonics of the cardiovascular pulse or to some other signals) or an estimate of the pulse rate that is otherwise inferior to an estimate of the pulse rate determined using the second signal during a period wherein the second signal can be used to determine the pulse rate. In such examples, the first and second signals, or pulse rates determined from the first and second signals, could be combined based on this relative difference between the signals, e.g., according to a weighted combination where the weightings corresponding to the first and second signal reflect the relative quality of each signal with respect to determining the pulse rate.

Additionally or alternatively, the second signal could, when available to determine the pulse rate, act as a 'ground truth' for the pulse rate of the cardiovascular pulse, and thus the pulse rate of the cardiovascular pulse could be determined, when the second signal is available to determine the pulse rate, based on the pulse rate determined from the second signal. This could include setting the determined pulse rate to be equal to the pulse rate determined from the second signal, using the second-signal pulse rate to select a pulse rate from a number of potential pulse rates that are determined based on the first signal (e.g., that correspond to determined frequencies of different spectral peaks or other contents of the first signal), or using a determined second signal pulse rate in some other way to determine a pulse rate for the cardiovascular pulse during a particular period of time. The pulse rate could be determined, for other time periods, based on the first signal during the other time periods in view of the pulse rates determined, based on the second signal, during the particular period of time. This could include using the pulse rate determined based on the second signal as a constraint for an acausal and/or retrospective determination of the pulse rate over time, resetting an ongoing estimate of the pulse rate (based, e.g., on ongoing detection of the first signal) to a pulse rate determined from the second signal when such a pulse rate can be determined from the second signal, or using the a pulse rate determined from the second signal in some other way, in combination with the first signal, to determine the pulse rate of a cardiovascular pulse over time.

In some examples, the first signal could be used to update, over time, an estimate of the pulse rate. The estimate of the pulse rate for a particular period of time, where the particular period of time is a period of time when the second signal can be used to determine a second-signal pulse rate, could be determined based on such a determined second-signal pulse rate (e.g., by setting the estimate equal to the second-signal pulse rate, by using the second-signal pulse rate to select a pulse rate from a number of potential pulse rates determined for the particular period of time based on the first signal). During subsequent (or preceding) periods of time, when the second signal is not available to determine a pulse rate, the estimate could continue to be updated based on the first signal.

An example of this is provided in FIG. 1A. A first signal related to a cardiovascular pulse is used to determine, for a first time period, a first set of pulse rates 110*a*. A second signal is detected, during a second period of time, that is related to the cardiovascular pulse and that can be used to determine a second-signal pulse rate. The timing of the second period of time, and the frequency of the second-signal pulse rate, are indicated in FIG. 1A by a circle (the second-signal pulse rate 120a). A second set of pulse rates 115a is determined, for a third period of time that is subsequent to the second period of time, based on the first signal and on the second-signal pulse rate.

As shown in FIG. 1A, the pulse rate is generally determined by the first signal, with the determined pulse rate gradually changing over time except when the second-signal pulse rate 120a is available, at which point the determined pulse rate jumps to correspond to the second-signal pulse rate 120a. Subsequent estimates of the pulse rate (i.e., 115a) gradually change over time from the second-signal pulse rate 120a. A variety of different algorithms or methods (e.g., an inertial filter, a Viterbi algorithm, a Kalman filter, a hidden Markov model) could be used to determine a pulse rate by updating previous estimates of the pulse rate or according to some other method based on previously detected values of the first signal and/or pulse rates determined for previous points in time based on the second signal.

As shown in FIG. 1A, the pulse rate (e.g., 110a, 115a) is determined for a particular point in time based on previously detected signals (e.g., previously detected values of a first signal, pulse rates determined for previous points in time based on previously detected values of a second signal); that is, pulse rates can be determined causally. Additionally or alternatively, a pulse rate can be determined, for a particular point in time, based on signals detected after the particular point in time. Such determinations can include retroactively determining a pulse rate and/or changing a determined pulse rate for previous points in time based on signals detected after the particular point in time.

Figure 1B:
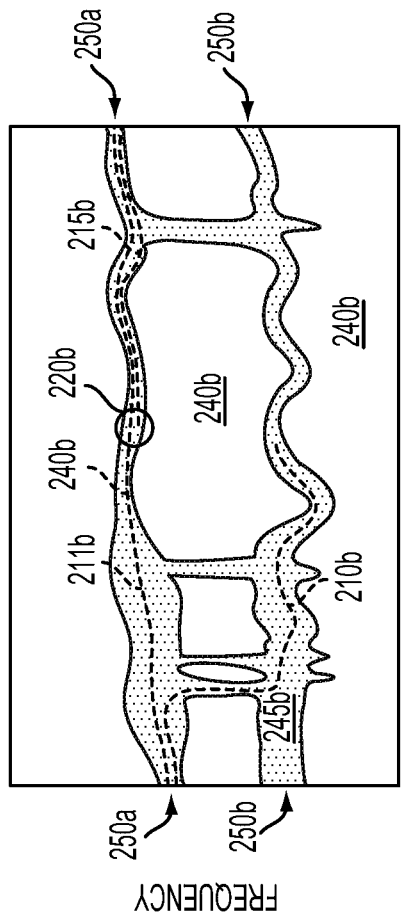
FIG. 1B is an example of predicted pulse rates over time.

An example of this is provided in FIG. 1B. A first signal related to a cardiovascular pulse is used to determine, for a first time period, a first set of pulse rates 130b. A second signal is detected, during a second period of time, that is related to the cardiovascular pulse and that can be used to determine a second-signal pulse rate. The timing of the second period of time, and the frequency of the second-signal pulse rate, are indicated in FIG. 1B by a circle (the second-signal pulse rate 120a). A second set of pulse rates 110b is determined, for the first period of time and for a third period of time that is subsequent to the second period of time, based on the first signal and on the second-signal pulse rate. Alternatively, the determination of the first set of pulse rates 130b could be omitted, and only the second set of pulse rates 110b could be determined for the first period of time once the second-signal pulse rate 120b has been determined and/or some other signals have been detected and/or determined.

As noted above, pulse rates can be determined, based on one or more signals related to a cardiovascular pulse and/or pulse rates determined from such signals, in a variety of ways. In some examples, a signal could be used to determine, for a particular period of time, an instantaneous estimate of the pulse rate and such a determined instantaneous pulse rate could be used to update (e.g., by a weighted combination of the instantaneous rate and the previous estimate, by applying an inertial filter, an alpha beta filter, or some other algorithm) an estimated pulse rate for a previous period of time to determine a pulse rate for the particular period of time. Such determinations can be constrained by pulse rates determined from further detected signals (e.g., pulse rates determined based on detected signals that are intermittently related to a cardiovascular pulse or otherwise intermittently available to determine a pulse rate) in a variety of ways. Estimated pulse rates could be constrained by being reset to such determined pulse rates or otherwise using such a determined pulse rate as a starting value or seed for the determination of pulse rates for other periods of time (e.g., for subsequent periods of time).

Additionally or alternatively, estimated pulse rates could be constrained by using a pulse rate determined from an intermittently available signal to choose a pulse rate from a number of potential pulse rates that are determined based on a further signal. For example, a number of potential pulse rates could be determined based on a first signal (e.g., a photoplethysmographic signal detected by detecting the absorption of light by blood in a portion of subsurface vasculature of a person). Such potential pulse rates could be determined in a variety of ways, e.g., by detecting peaks, maxima, or other features of a power spectrum or other spectral content determined from the first signal, by determining the instantaneous frequencies of a number of phase locked loops that receive the first signal as an input, or using some other methods. A second-signal pulse rate, determined based on a detected second signal (e.g., an electrocardiographic signal that is intermittently available when a user contacts electrodes of a sensor), could then be used to select one of the potential pulse rates. Such a selection could be performed by determining a difference between each of the potential pulse rates and the second-signal pulse rate and selecting the potential pulse rate that has the smallest difference.

Figure 2A:
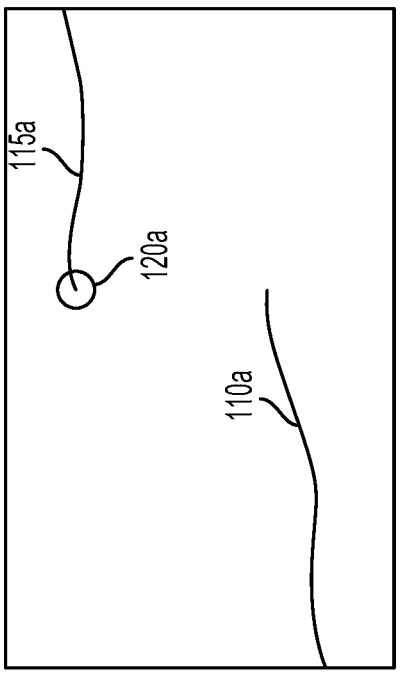
FIG. 2A is an example of predicted pulse rates over time.

An example of this is provided in FIG. 2A. A first signal related to a cardiovascular pulse is used to determine a first 210a, second 213a, and third 215a sets of potential pulse rates. A second signal is detected that is related to the cardiovascular pulse during a particular period of time and that is used to determine, for the particular period of time, a second-signal pulse rate. The timing of the particular period of time, and the frequency of the second-signal pulse rate, are indicated in FIG. 2A by a circle (the second-signal pulse rate 220a). The second-signal pulse rate 220a is then used to select one of the sets of potential pulse rates 210a, 213a, 215a based on a difference between the second-signal pulse rate 220a and pulse rates of the sets of potential pulse rates corresponding to the particular period of time. As shown in FIG. 2A, the first set of potential pulse rates 210a is selected as the first set of potential pulse rates 210a, during the particular period of time, has a difference from the second-signal pulse rate 220a that is less than the difference between the second-signal pulse rate 220a and pulse rates, during the particular period of time, of the other two sets of potential pulse rates 213a, 215a.

A detected signal could be used in a variety of ways to determine pulse rates. Time-domain methods could be used to detect the timing, rate of occurrence, or other properties of time-domain features of a detected signal, e.g., one or more instances of a feature of the signal (e.g., a zero crossing, a local maximum, a local minimum, a QRS complex of an electrocardiographic signal, a triangular peak of a photoplethysmographic signal) could be detected within the signal and the timing of such detected features could be used to determine a pulse rate based on the signal. In some examples, a filter, controller, oscillator, or other structure could be applied to the signal to detect a pulse rate. For example, one or more phase-locked loops could receive the detected signal as an input and could lock in to oscillating contents of the detected signal, allowing the pulse rate to be determined from the instantaneous frequencies of the one or more phase locked loops.

Additionally or alternatively, spectral content of the signal (e.g., a Fourier transform, a power spectrum, a spectrogram) could be determined and used to determine one or more pulse rates. For example, peaks or other features could be determined from a power spectrum, Fourier transform, or other spectral content determined from samples of the signal detected during a particular period of time and the frequency of such determined peaks or other features could be used to determine a pulse rate for the particular period of time. In some examples, a number of potential pulse rates could be determined for the particular period of time based on the frequencies of corresponding different peaks or other features of the spectral content. One of the potential pulse rates could be selected for the particular period of time based on some further information corresponding to the particular period of time, e.g., based on a second-signal pulse rate determined for the particular period of time based on a second signal that is detected during the particular period of time.

Further, a plurality of pulse rates could be determined, for a corresponding plurality of periods of time, based on a spectrogram, a plurality of power spectra, or some other spectral content determined for the plurality of different periods of time. For example, such spectral content could be used to determine sequences of pulse rates over time that maximize the likelihood of the sequence, that minimize a rate of change of the determined sequence of pulse rates over time, or according to some other considerations. Such a sequence of pulse rates could be determined, based on determined spectral content, using the Viterbi algorithm, a hidden Markov model, or some other methods. Further, such determined sequences could be constrained by additional information about a cardiovascular pulse, e.g., by a pulse rate determined, for a particular period of time, based on a further signal that is related to the cardiovascular pulse during the particular period of time (e.g., an electrocardiographic signal detected from electrodes that are in contact with skin of opposite arms of a person during the particular period of time). Such additional information could be used as an initial value for determining further pulse rates based on the spectral content (e.g., a sequence of pulse rates could be reset to such a value) or could be used to constrain the determined pulse rates in some other way.

Figure 2B:
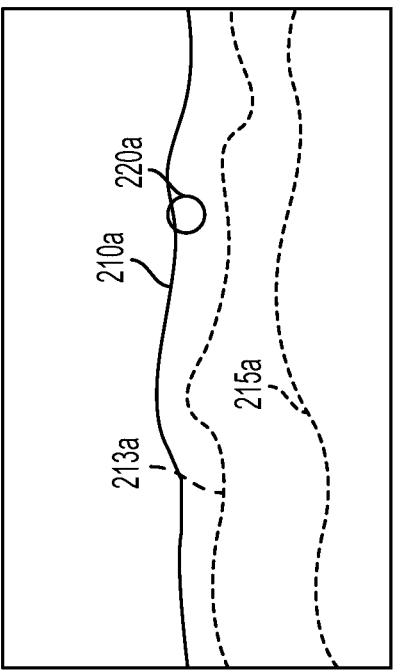
FIG. 2B is an example of predicted pulse rates over time.

FIG. 2B provides an illustrative example of such spectral content and pulse rates determined therefrom. FIG. 2B illustrates spectral content determined from a first signal over time, showing high-energy regions 245b and low-energy regions 240b corresponding to ranges of frequencies that, during different periods of time, represent more or less, respectively, of the frequency content of the first signal. The high-energy regions 245b could correspond to high-magnitude regions of a spectrogram, high-magnitude portions of a plurality of power spectra or Fourier transforms corresponding to different periods of time, or to some other property of a determined spectral content of the first signal that corresponds to ranges of frequency that may include the pulse rate of the cardiovascular pulse during different periods of time. The high-energy regions 245b exhibit two tracks, 250a and 250b, that could correspond to regularly repeating patterns or other oscillating contents of the first signal, e.g., repeating patterns corresponding to the cardiovascular pulse (e.g., a repeating pattern of light absorption over time corresponding to the volume of blood in a portion of subsurface vasculature over time), harmonics of such patterns, repetitive motion of a sensor and/or of a person (e.g., a repeated signal related to repeated motion of a person due to walking or exercise), or some other repeating content. These tracks are connected at a number of points in time by vertical high-energy regions 245b; such vertical regions could correspond to noise in the first signal during periods of time when the first signal includes such noise, e.g., when a sensor that is detecting the first signal is displaced relative to a portion of subsurface vasculature or other tissue.

Pulse rates for the cardiovascular pulse could be determined based on determined spectral content (e.g., a spectrogram, one or more power spectra or Fourier transforms, or some other content corresponding to, e.g., the regions 240b, 245b illustrated in FIG. 2B) in a variety of ways. In some examples, the pulse rates can be determined as a sequence, e.g., using the alpha-beta filter, the Viterbi algorithm, an inertial filter, or some other method for determining a pulse rate for a particular period of time based on spectral content for the particular point of time and pulse rates determined for proximate periods of time and/or spectral content determined for the proximate periods of time. Such determinations could be causal (that is, a pulse rate for a particular period of time is determined based on detected signals or information determined therefrom detected during the particular period of time and/or prior to the particular period of time) or acausal (that is, a pulse rate for a particular period of time is determined based on signals detected during, before, and/or after the particular point in time and/or information determined from such detected signals).

Pulse rates could be determined based on pulse rates determined from further detected signals, e.g., based on a pulse rate determined for a particular period of time based on a detected signal that is related to the cardiovascular pulse during the particular period of time. As shown in FIG. 2B, a first signal that is related to a cardiovascular pulse is detected and used to determine spectral content of the first signal (illustrated by the regions 240b, 245b). A second signal is detected, during a particular period of time, that is related to the cardiovascular pulse and that can be used to determine a second-signal pulse rate. The timing of the particular period of time, and the frequency of the second-signal pulse rate, are indicated in FIG. 2B by a circle (the second-signal pulse rate 220b).

The second-signal pulse rate 220b could be used to determine pulse rates only for periods of time subsequent to the particular period of time; that is, the second-signal pulse rate 220b could be used causally, in combination with the spectral content of the first signal, to determine pulse rates. This could include determining pulse rates based on the spectral content unless a second-signal pulse rate is available, at which time the determined pulse rate will be reset to the value of the second-signal pulse rate or otherwise changed based on the second-signal pulse rate. This is depicted, by way of example, in FIG. 2B by a sequence of prior pulse rates 210b that are determined for periods of time prior to the particular period of time during which the second-signal pulse rate 220b is available. The determined pulse rate is then set to the second-signal pulse rate 220b for the particular period of time. Pulse rates for subsequent periods of time are determined from the second-signal pulse rate 220b, depicted in FIG. 2B by a sequence of subsequent pulse rates 215b.

Alternatively, the second-signal pulse rate 220b could be used to determine pulse rates for periods of time before and after the particular period of time; that is, the second-signal pulse rate 220b could be used acausally, in combination with the spectral content of the first signal, to determine pulse rates. For example, the second-signal pulse rate 220*b* could be used as a constraint on the pulse rate determined for the particular period of time when the second-signal pulse rate 220*b* is available and pulse rates for prior and subsequent periods of time could be determined based on the second-signal pulse rate 220*b* (e.g., using the second-signal pulse rate 220*b* as a starting value or seed). This is depicted in FIG. 2B by a further sequence of determined pulse rates 240*b*.

A variety of physiological or other signals related to a cardiovascular pulse or to some other oscillating or otherwise repeating pattern could be detected and used to determine a cardiovascular pulse rate or other frequency or rate as described herein. In some examples, such signals could be substantially consistently available for determining the pulse rate, e.g., due to a stable contact and/or relative location of a sensor and a skin surface, a portion of subsurface vasculature, or some other portion of tissue measured having a property measured by the sensor, due to noise characteristics of the sensor and/or of a physical variable measured by the sensor, or due to some other factors. Such sensors could include photoplethysmographic sensors (that is, sensors configured to detect a signal related to a cardiovascular pulse by illuminating a portion of subsurface vasculature and detecting the intensity or other properties of the light responsively reflected, scattered, or otherwise emitted from the portion of subsurface vasculature), acoustical sensors (e.g., sensors configured to detect heart noises or other sounds related to a cardiovascular pulse), ultrasound sensors (e.g., sensors configured to emit ultrasound energy into a portion of subsurface vasculature and to detect the velocity or other properties of blood flow in the portion of subsurface vasculature over time based on properties of the reflected ultrasound energy), or some other sensors.

As noted above, signals detected by such sensors could be augmented intermittently by further signals that are not substantially continuously related to a cardiovascular pulse and thus may not be continuously available to determine a pulse rate of the cardiovascular pulse. Such signals could, during intermittent periods of time, be detected and used to determine pulse rates that could be used to improve the ongoing determination of pulse rates using some other detected signal (e.g., by resetting the ongoing determination of the pulse rate to a value of the pulse rate determined using the intermittent signal, by using the intermittent signal to select one of a set of potential pulse rates determined based on the other detected signal, or according to some other method(s) described herein).

Such further signals could be detected using sensors that are in inconsistent contact with a body, e.g., such that the signal can be used to determine a pulse rate only when the sensor is in steady contact with a body. Such a sensor could include two or more electrodes configured to detect an electrocardiographic signal, a skin conductance signal, or some other electrical signal related to a cardiovascular pulse when the electrodes of the sensor are in electrical contact with respective locations of skin of the body. Such a sensor could include an accelerometer or other motion sensor configured to detect displacement, acceleration, or other motions of the sensor such that, when the sensor is in consistent contact with skin and there is minimal absolute motion of the skin, displacement or other motion of the sensor is related to the cardiovascular pulse, e.g., due to displacements of skin overlying a portion of subsurface vasculature that are related to changes in the volume and/or pressure of blood in the portion of subsurface vasculature.

Such further signals could be detected and assessed to determine whether a pulse rate can be reliably determined from the further signal. This could include determining a power level of the detected signal, a signal to noise ratio of the detected signal (e.g., a power in frequency bands corresponding to a signal of interest divided by total signal power), a power of the signal within one or more frequency bands (e.g., within frequency bands related to noise content of the signal), a variability of a pulse rate or pulse period determined based on the signal, a quality and/or presence of a feature in the signal (e.g., a QRS complex in the signal), or some other determination related to whether a pulse rate can be reliably determined from the signal. Additionally or alternatively, some additional variable related to the further signal could be detected and used to determine whether a pulse rate can be reliably determined from the further signal. For example, an impedance between electrodes of an electrocardiogram sensor, a pressure or force between a sensor and a skin surface, or some other variables related to the use of a sensor to detect the further signal could be detected and used to determine whether a pulse rate can be reliably determined from the further signal.

In some examples, the actions of a person (e.g., a person whose cardiovascular pulse is being detected) could result in a signal being related to a cardiovascular pulse such that a pulse rate can be reliably determined from the signal. For example, the person could place a sensor into contact with skin or with some other body part, the person could apply a force to ensure that a sensor is in reliable contact with the body part, the person could move a body part to be in contact with a sensor, or the person could perform some other action such that a sensor is able to detect a signal that is related to a cardiovascular pulse. For example, a person could place one or more skin surfaces in contact with respective electrodes of a sensor to facilitate the detection of an electrocardiographic signal, a skin conductance, or some other electrical signal related to a cardiovascular pulse.

As an example, a wearable device could be configured to mount to a first wrist (e.g., the left wrist) of the wearer and to have a first electrical contact configured to contact a first skin location on the first wrist. The wearable device could further include a second electrical contact configured to be contacted by a second skin location of the wearer. That is, the wearer could move a portion of the wearer's body (e.g., a right hand) proximate to the wearable device such that a second skin location (e.g., a finger, hand, or wrist location of the arm of the wearer opposite the arm to which the wearable device is mounted) is in contact with the second electrical contact of the wearable device. In this way, the wearable device could enable periodic extraction of electrocardiographic signals from voltage fluctuations between the two skin locations (e.g., between a wrist location of the left arm and a finger location of the right arm). Such a wearable device could be configured in the form of a wristwatch or other wrist-mounted device (i.e., having a central housing (on or within which could be mounted first and/or second electrical contacts) mounted to the wrist by e.g., a strap or band configured to encircle the wrist) and could include means for performing additional functions, e.g., indicating a time and/or pulse rates to the wearer. Such a device could additionally include other sensors configured to detect signals related to the cardiovascular pulse, e.g., a photoplethysmographic sensor. Pulse rates could be determined based on signals detected by the other sensor(s) and such determined pulse rates could be adjusted, reset, or otherwise improved when the electrocardiographic signals are available for determination of the pulse rate (e.g., when the wearer contacts the second electrode with skin of the opposite arm).

Figure 3A:
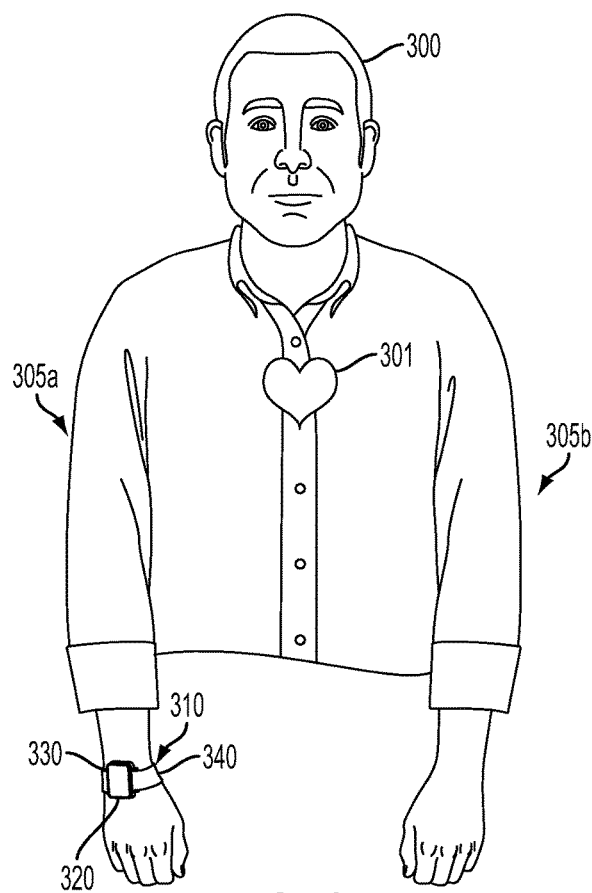
FIG. 3A is a view of a person wearing an example wearable device.

FIG. 3A illustrates such an example wearable device 310 mounted to a wrist of a first arm 305a of a wearer 100 during a first period of time. The wearable device 310 includes a housing 320 mounted to the wrist of the first arm 305a by a mount 340 (e.g., a strap or band). The wearable device further includes first (not shown) and second 330 electrical contacts. The first electrical contact is disposed on an inside (i.e., wrist-facing) side of the housing 320 and configured to contact skin at a first external body surface (i.e., skin of the wrist of the first arm 305a) when the housing 320 is mounted on the wrist of the first arm 305a. The second electrical contact 330 is configured to be contacted by skin of a second external body surface (e.g., by finger, hand, wrist, or other skin of a second arm 305b of the wearer 300). The wearable device 310 additionally includes electronics (e.g., a signal conditioner or other elements of a sensor, not shown) electrically connected to the first and second 330 electrical contacts and configured to extract an electrocardiographic signal (related to a cardiovascular pulse of the heart 301 of the wearer 300) from voltage fluctuations between the first and second 330 electrical contacts.

Figure 3B:
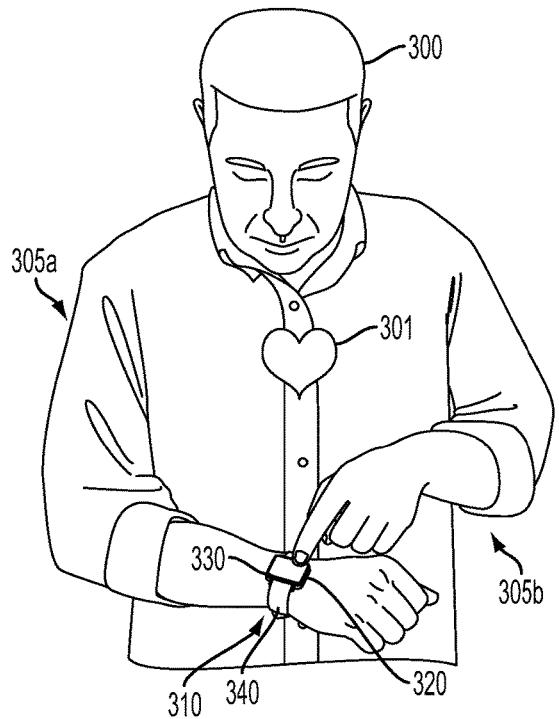
FIG. 3B is a view of the person and wearable device illustrated in FIG. 3A, when the user is contacting the wearable device with a finger.

FIG. 3B illustrates the wearable device 310 and wearer 300 during a second period of time when the wearer 300 is positioning skin of a finger of the second arm 305b in contact with the second electrical contact 330. In this state, electronics (e.g., a signal conditioner) of the wearable device 310 could extract an electrocardiographic signal related to the cardiovascular pulse of the wearer's 300 heart 301 during the second period of time from voltage fluctuations between the first and second 330 electrical contacts.

Figure 3C:
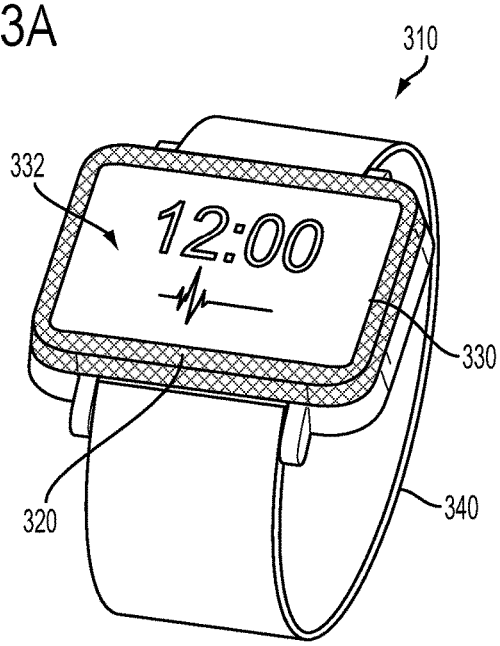
FIG. 3C is a perspective view of an example wearable device.

FIG. 3C illustrates the wearable device 310 in detail. The housing 320 has an outside surface that is away from the first external surface of the body and an inside surface (not shown) that is toward and/or in contact with the first external surface of the body when the housing 320 is positioned on the first external surface of the body. A user interface 332 is disposed on the outside surface of the housing 320. The second electrical contact 330 is disposed along an edge of the outside surface of the housing 310d completely enclosing the user interface 332. Other configurations of a wearable device as described herein are anticipated.

Note that descriptions of the determination of pulse rates based on samples of detected signals using methods herein are intended as non-limiting illustrative examples of the determination of frequencies and/or rates of oscillating and/or repeating contents of a variety of detected signals. Such methods could be used to determine a rate of breathing, a rate of locomotion or other repeated action or motion, or some other rate or frequency that could be determined based on a detected physiological signal or some other detected signal (e.g., a strain detected using a chest strap breathing sensor, an accelerometer mounted to a body part). Further, systems and methods described herein could be used to determine frequencies or rates of such processes in an animal. Systems and methods described herein could be used to determine frequencies or rates of contents of signals detected from a natural environment (e.g., a frequency of cyclical water flows in a marsh, lake or stream), an artificial environment (e.g., a frequency of repeating patterns in a detected rate of inflow into a water treatment process), or some other environment of interest.

III. EXAMPLE DEVICES

One or more devices or systems could be configured to determine a pulse rate of a cardiovascular pulse (or to determine a rate or frequency of some other process or pattern or interest) based on signals detected using one or more sensors. As noted elsewhere herein, one or more of the sensors could detect a signal that is intermittently related to the cardiovascular pulse (or other process of interest) and thus may be used, for periods of time when the signal is related to the cardiovascular pulse, to determine a pulse rate and such a determined pulse rate could be used, in combination with other detected signals, to reset an ongoing sequence of determined pulse rates, to select one of a set of potential pulse rates determined based on the other detected signals, to serve as a seed or initial value for determination of pulse rates for other periods of time, or according to some other method to determine pulse rates of the cardiovascular pulse.

The sensors used to detect such signals could be disposed in a single device (e.g., a single wearable or otherwise body-mountable device) or in multiple devices. For instance, a first device that is securely mountable to a wrist could include a first sensor (e.g., a photoplethysmographic sensor) that is configured to substantially continuously detect a signal related to a cardiovascular pulse (e.g., an amount of absorption of light by blood in a portion of subsurface vasculature that changes over time as the volume of blood in the portion of subsurface vasculature changes) when the first device is mounted to the wrist. A second device could include a necklace, a garment, a blanket, or some other elements that are configured to be loosely in contact with a body or otherwise intermittently able to access a signal that is related to the cardiovascular pulse (e.g., to access an electrocardiographic signal when electrodes of the device are in reliable contact with skin, to detect an acceleration of the device that is related to the cardiovascular pulse when the device is in reliable contact with skin). Outputs from both devices could be combined to determine pulse rates of the cardiovascular pulse. Such determinations could be performed by controllers or other elements in one or more devices of such multiple-device systems, or by a controller that is part of some further system or device that is in communication with the devices including such sensors (e.g., by a cloud computing system).

Figure 4:
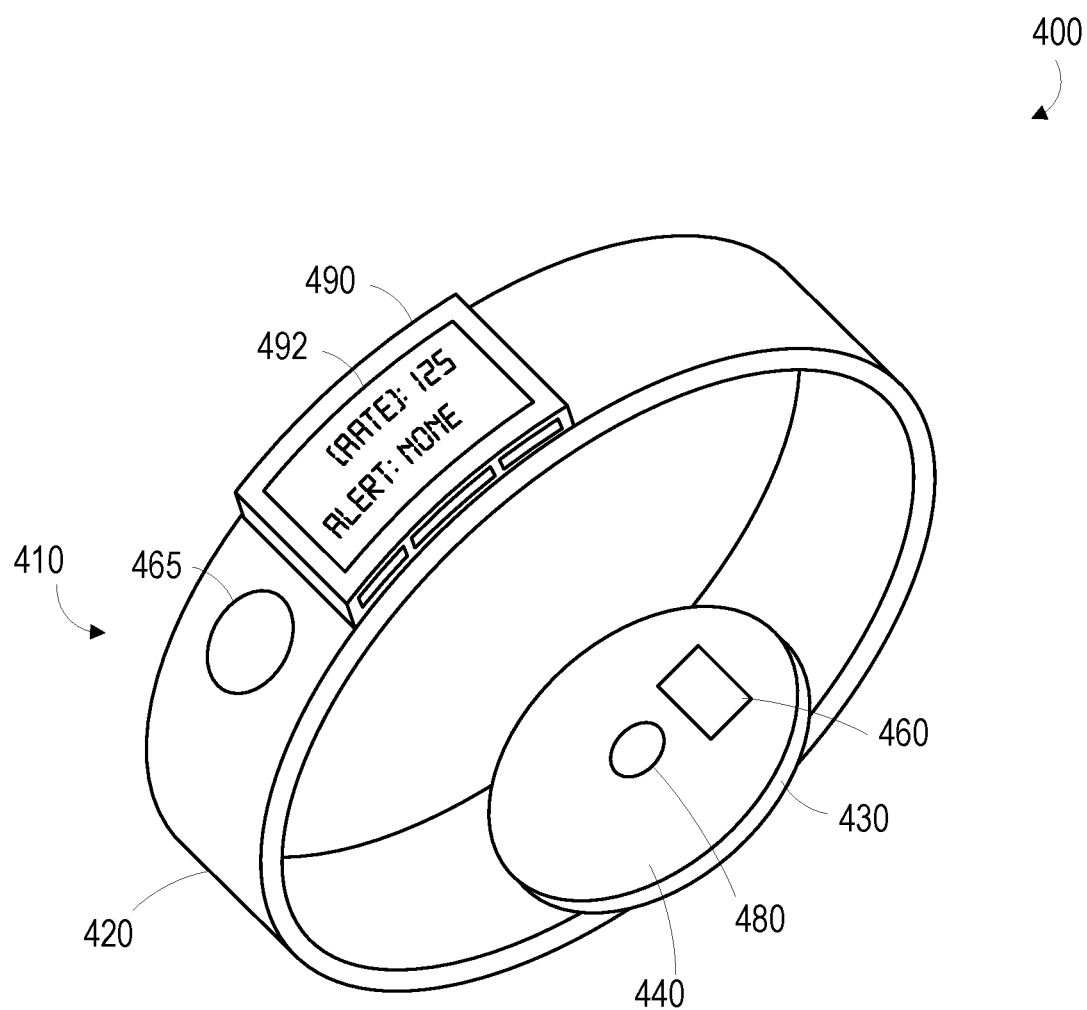
FIG. 4 is a perspective view of an example wearable device.

An example of a wearable device 400 that can operate at least one sensor to detect a signal that is at least intermittently related to a cardiovascular pulse is illustrated in FIG. 4. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where a signal related to the cardiovascular pulse may be detected (e.g., proximate a portion of subsurface vasculature or some other tissue containing pulsatile blood flow, proximate one or more skin locations from which an electrocardiographic signal may be extracted), the qualification of which will depend on the type of detection system used. The device may be placed in close proximity to skin or tissue, but need not be touching or in intimate contact therewith. A mount 410, such as a belt, wristband, ankle band, etc. can be provided to mount the device at, on or in proximity to the body surface. The mount 410 may prevent the wearable device from moving relative to the body to reduce measurement error and noise. In one example, shown in FIG. 4, the mount 410, may take the form of a strap or band 420 that can be worn around a part of the body. Further, the mount 410 may be an adhesive substrate for adhering the wearable device 400 to the body of a wearer.

A measurement platform 430 is disposed on the mount 410 such that it can be positioned on the body where subsurface vasculature is easily observable or where some other signal of interest may be detected. An inner face 440 of the measurement platform is intended to be mounted facing to the body surface. The measurement platform 430 may house a data first sensor 480, which may be configured to detect one or more signals related to a cardiovascular pulse. For example, the first sensor 480 may include an optical sensor that is configured to detect a degree of absorption of light at one or more wavelengths by blood in a portion of subsurface vasculature over time (e.g., by illuminating the portion of subsurface vasculature and detecting an intensity or other properties of light responsively reflected by, scattered by, or otherwise emitted from the portion of subsurface vasculature). In another example, the first sensor 480 may include an accelerometer, a pressure sensor, or some other sensor configured to detect a blood pressure in the portion of subsurface vasculature, to detect a displacement of the skin surface related to changes in the volume or pressure of blood in the portion of subsurface vasculature, or to detect some other physical variable related to a cardiovascular pulse.

The measurement platform 430 may include multiple such sensors, and the signals detected using the sensor(s) could be substantially continuously related to a cardiovascular pulse or could be intermittently related to the cardiovascular pulse (e.g., when the absolute or relative (to a target tissue, e.g., skin surface, portion of subsurface vasculature) motion of the sensor is minimal, when the sensor is in consistent contact with skin or with some other tissue). Further, the measurement platform 430 may include elements of sensors that are configured to operate to detect a signal that is related to the cardiovascular pulse when a wearer performs some action. For example, the measurement platform 430 includes a first electrode 460 that is configured to be in contact with skin of the wrist when the wearable device 400 is mounted to the wrist. The wearable device also includes a second electrode 465 that is disposed on the band 420 and that can be contacted by skin of an opposite arm (e.g., skin of a fingertip) of a wearer. When the device 400 is mounted to a wrist such that the first electrode 460 is in contact with skin of the wrist and the second electrode 465 is being contacted by skin of the opposite arm, an electrical potential signal related to the cardiovascular pulse (e.g., an electrocardiographic signal) could be detected by a sensor of the device 400 using the electrodes 460, 465.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of the measured physiological parameters, for instance, a determined cardiovascular pulse rate.

Figure 5:
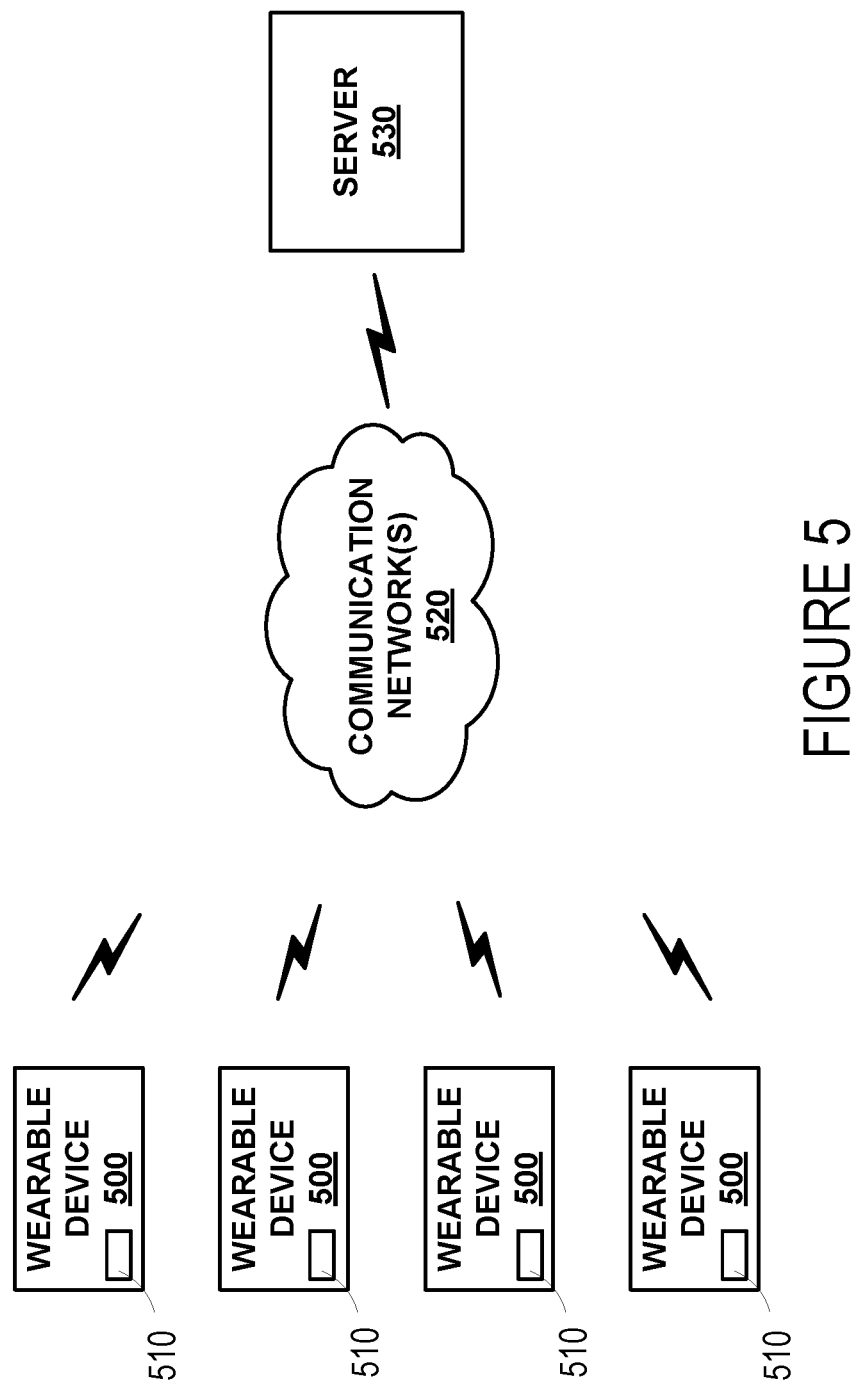
FIG. 5 is a block diagram of an example system that includes a plurality of wearable devices in communication with a server.

FIG. 5 is a simplified schematic of a system including one or more wearable devices 500. The one or more wearable devices 500 may be configured to transmit data via a communication interface 510 over one or more communication networks 520 to a remote server 530. In one embodiment, the communication interface 510 includes a wireless transceiver for sending and receiving communications to and from the server 530. In further embodiments, the communication interface 510 may include any means for the transfer of data, including both wired and wireless communications. For example, the communication interface may include a universal serial bus (USB) interface or a secure digital (SD) card interface. Communication networks 520 may be any one of may be one of: a plain old telephone service (POTS) network, a cellular network, a fiber network and a data network. The server 530 may include any type of remote computing device or remote cloud computing network. Further, communication network 520 may include one or more intermediaries, including, for example wherein the wearable device 500 transmits data to a mobile phone or other personal computing device, which in turn transmits the data to the server 530.

In addition to receiving communications from the wearable device 500, such as collected physiological parameter data and data regarding health state as input by the user, the server may also be configured to gather and/or receive either from the wearable device 500 or from some other source, information regarding a wearer's overall medical history, environmental factors and geographical data. For example, a user account may be established on the server for every wearer that contains the wearer's medical history. Moreover, in some examples, the server 530 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding a pulse rate of a cardiovascular pulse of a user based on information received from one or more of the wearable devices 500 that are associated with the user. This could include receiving signals detected by multiple sensors of a single wearable device 500 and/or receiving signals from multiple devices 500 and using the received signals to determine the pulse rates. The server may also be configured to make determinations regarding drugs or other treatments received by a wearer of one or more of the devices 500 and, at least in part, the physiological parameter data and the indicated health state of the user. From this information, the server may be configured to derive an indication of the effectiveness of the drug or treatment. For example, if a wearer is prescribed a drug intended to treat tachycardia, but the server receives data from the wearable device(s) indicating (based on determined pulse rates) that the wearer's heart rate has remained elevated over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. EXAMPLE ELECTRONICS PLATFORM

Figure 6:
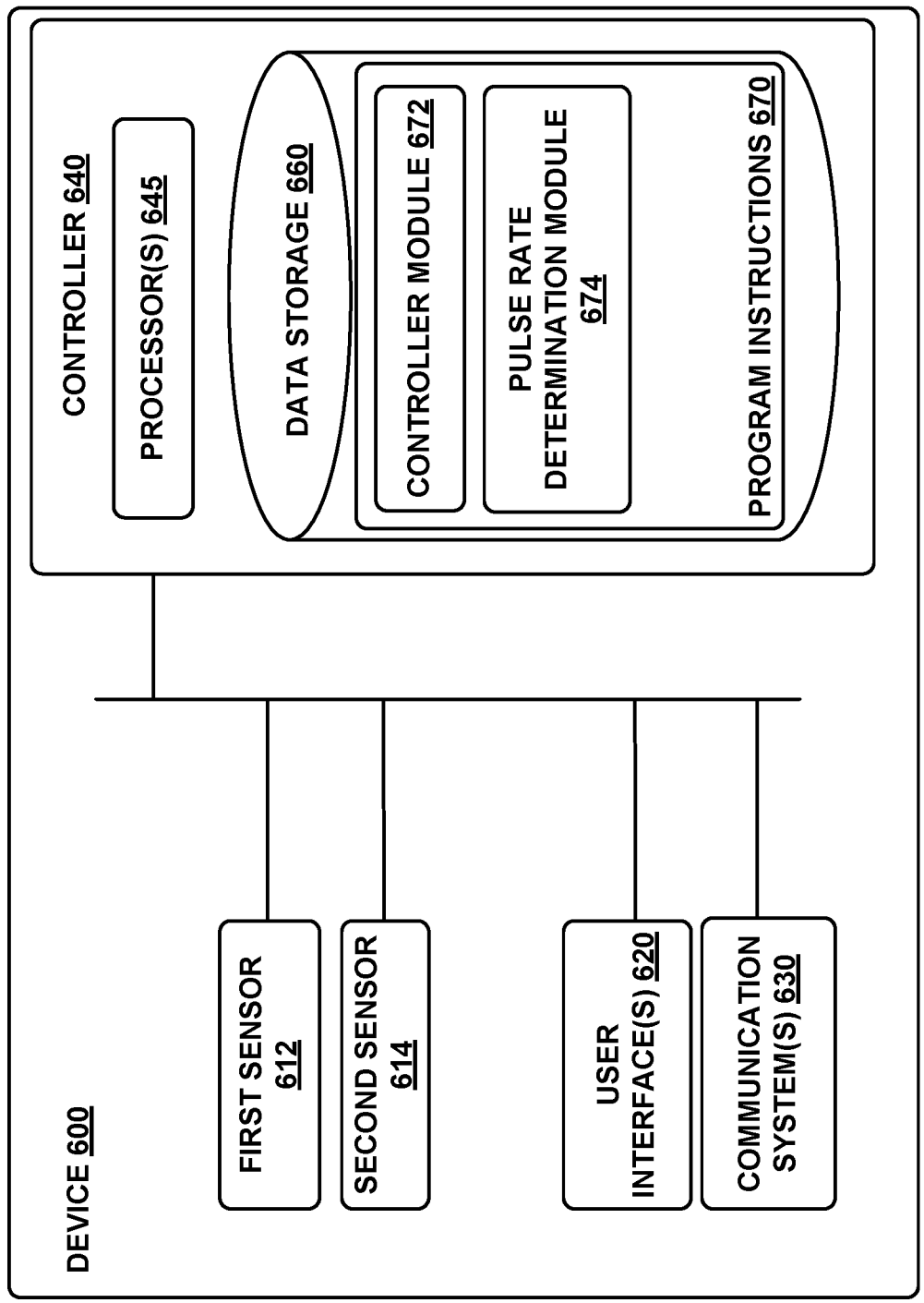
FIG. 6 is a functional block diagram of an example device.

FIG. 6 is a simplified block diagram illustrating the components of a device 600, according to an example embodiment. Device 600 may take the form of or be similar to the devices 310, 400 shown in FIGS. 3A, 3B, 3C and 4. That is, device 600 may take the form of a wrist-mountable or otherwise body-mountable device. Device 600 may also take other forms, e.g., could take the form of a device configured to be maintained in proximity to an environment of interest (e.g., a body part) by a user or operator of the device 600 or by a frame or other supporting structure. Device 600 could also take the form of a device configured to signals of interest from some other environment, for example, a body of an animal or some other environment containing a parameter or variable that contains an oscillating pattern having a frequency or rate that could be detected according to the methods described herein. Device 600 also could take other forms.

In particular, FIG. 6 shows an example of a device 600 having a first sensor 612, a second sensor 614, a user interface 620, communication system(s) 630 for transmitting data to a remote system, and controller 640. The components of the device 600 may be disposed on a mount or on some other structure for mounting the device to enable stable detection of one or more signals related to a cardiovascular pulse or other process of interest, for example, around a wrist of a wearer such that signals related to a portion of subsurface vasculature or other target tissue are detectable.

Controller 640 may be provided as a computing device that includes one or more processors 645. The one or more processors 645 can be configured to execute computer-readable program instructions 670 that are stored in the computer readable data storage 660 and that are executable to provide the functionality of a device 600 described herein.

The computer readable data storage 660 may include or take the form of one or more non-transitory, computer-readable storage media that can be read or accessed by at least one processor 645. The one or more computer-readable storage media can include volatile and/or non-volatile storage components, such as optical, magnetic, organic or other memory or disc storage, which can be integrated in whole or in part with at least one of the one or more processors 645. In some embodiments, the computer readable data storage 660 can be implemented using a single physical device (e.g., one optical, magnetic, organic or other memory or disc storage unit), while in other embodiments, the computer readable data storage 660 can be implemented using two or more physical devices.

The first 612 and second 614 sensors are configured to detect respective first and second signals. As noted elsewhere herein, the first sensor 612 could detect a signal that is substantially continuously related to a cardiovascular pulse of a person such that the first signal can be used substantially continuously to determine a pulse rate of the cardiovascular pulse. The second sensor 614 could detect a second signal that is intermittently related to the cardiovascular pulse such that the second signal can be used to determine pulse rates for the cardiovascular pulse for those periods of time when the second signal is related to the cardiovascular pulse (e.g., when a wearer contacts electrodes of the second sensor 614 with skin of the wearer, when the second sensor 614 is in stable contact with a body). The first 612 and second 614 sensors could be provided on or within a single housing of the device 600 or within multiple housings (e.g., connected using a cable or other interconnection). The first 612 and second 614 sensors could include any of the types of sensors described elsewhere herein to detect signals that are at least intermittently related to a cardiovascular pulse or other repeating process of interest.

The program instructions 670 stored on the computer readable data storage 660 may include instructions to perform any of the methods described herein. For instance, in the illustrated embodiment, program instructions 670 include a controller module 672 and a pulse rate determination module 674.

The controller module 672 can include instructions for operating the first 612 and second 614 sensors. For example, the controller module 672 may include instructions for operating a light source and light sensor of the first sensor 612 at a plurality of points in time to obtain a respective plurality of samples of a photoplethysmographic signal. In another example, the controller module 672 may include instructions for operating an accelerometer, a pressure sensor, or some other sensor to measure signals related to a cardiovascular pulse. The controller module 672 may include instructions for operating one or both of the sensors 612, 614 to detect a signal that is not directly related to a cardiovascular pulse but that may be related to the operation of the sensors 612, 614 to detect such signals, e.g., to detect an impedance between electrodes that may be used, by the second sensor 614, to detect an electrocardiographic signal related to the cardiovascular pulse. In some examples, the controller module 672 may operate an analog-to-digital converter (ADC) to sample one or more signals (e.g., amplifier outputs) generated by the first 612 and/or second 614 sensors to obtain sets of samples of the signals detected during one or more periods of time.

The controller module 672 can also include instructions for operating a user interface 620. For example, controller module 672 may include instructions for displaying data collected by the controller module 672 and analyzed by the pulse rate determination module 674. Further, controller module 672 may include instructions to execute certain functions based on inputs accepted by the user interface 620, such as inputs accepted by one or more buttons or touchscreen displays disposed on the user interface.

Pulse rate determination module 674 may include instructions for analyzing data (e.g., sets of samples obtained from signals detected by the sensors 612, 614) to determine cardiovascular pulse rates, to determine based on such determined pulse rates or other information if a medical condition is indicated (e.g., an arrhythmia, a heart attack, a cardiac arrest), or other analytical processes relating to the environment proximate to the device 600. In particular, the pulse rate determination module 674 may include instructions for determining spectral contents, pulse rates, or other information based on samples of the signals detected by the sensors 612, 614. In particular, the pulse rate determination module 674 may include instructions for combining the signals detected using both of the sensors 612, 614 when such signals are related to a cardiovascular pulse (e.g., when electrodes of the second sensor 614 are in reliable contact with skin of a wearer such that an electrical potential between the electrodes is related to the cardiovascular pulse). The pulse rate determination module 674 could further include instructions for determining that a signal detected by one of the sensors 612, 614 is related to the cardiovascular pulse during a particular period of time, e.g., by detecting the presence or some other quality of features (e.g., QRS complexes of an electrocardiographic signal, peaks of a photoplethysmographic signal) in the signal, by determining a degree of variability of pulse timing or pulse rates determined from the signal, by determining a signal-to-noise ratio or other noise information about the signal, or using some other methods.

Some of the program instructions of the controller module 672 and the pulse rate determination module 674 may, in some examples, be stored in a computer-readable medium and executed by a processor located external to the device 600. For example, the device 600 could be configured to operate one or both of the sensors 612, 614 (or to otherwise generate or obtain a plurality of samples of a signal related to a cardiovascular pulse) and then transmit related data to a remote server, which may include a mobile device, a personal computer, the cloud, or any other remote system, for further processing (e.g., for the determination of pulse rates and/or frequencies of oscillating patterns in the signal(s) using methods described herein). Additionally or alternatively, the device 600 could receive, using the communication system(s) 630, samples of a signal related to the cardiovascular pulse from some other device (e.g., a device that is part of a necklace, a garment, a blanket, or some other object) and a cardiovascular pulse could be determined by the device 600 using such received samples in combination with information (e.g., samples) of signals detected by the sensors 612, 614 of the device 600.

User interface 620 could include indicators, displays, buttons, touchscreens, head-mounted displays, and/or other elements configured to present information about the device 600 to a user and/or to allow the user to operate the device 600. Additionally or alternatively, the device 600 could be configured to communicate with another system (e.g., a cellphone, a tablet, a computer, a remote server) and to present elements of a user interface using the remote system.

The user interface 620 could be disposed proximate to the sensors 612, 614 or other elements of the device 600 or could be disposed away from other elements of the device 600 and could further be in wired or wireless communication with the other elements of the device 600. The user interface 620 could be configured to allow a user to specify some operation, function, or property of operation of the device 600. The user interface 620 could be configured to present a determined pulse rate or some other health state of a wearer of the device 600, or to present some other information to a user. Other configurations and methods of operation of a user interface 620 are anticipated.

Communication system(s) 630 may also be operated by instructions within the program instructions 670, such as instructions for sending and/or receiving information via a wireless antenna, which may be disposed on or in the device 600. The communication system(s) 630 can optionally include one or more oscillators, mixers, frequency injectors, etc. to modulate and/or demodulate information on a carrier frequency to be transmitted and/or received by the antenna. In some examples, the device 600 is configured to indicate an output from the controller 640 by transmitting an electromagnetic or other wireless signal according to one or more wireless communications standards (e.g., Bluetooth, WiFi, IRdA, ZigBee, WiMAX, LTE). In some examples, the communication system(s) 630 could include one or more wired communications interfaces and the device 600 could be configured to indicate an output from the controller 640 by operating the one or more wired communications interfaces according to one or more wired communications standards (e.g., USB, FireWire, Ethernet, RS-232).

In some examples, obtained samples of a signal or other physiological property or parameter of interest, determined pulse rates, or other information generated by the device 600 may additionally be input to a cloud network and be made available for download by a user's physician. Analyses may also be performed on the collected data, such as estimates of pulse rate variability, arrhythmia, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

V. ILLUSTRATIVE METHODS

Figure 7:
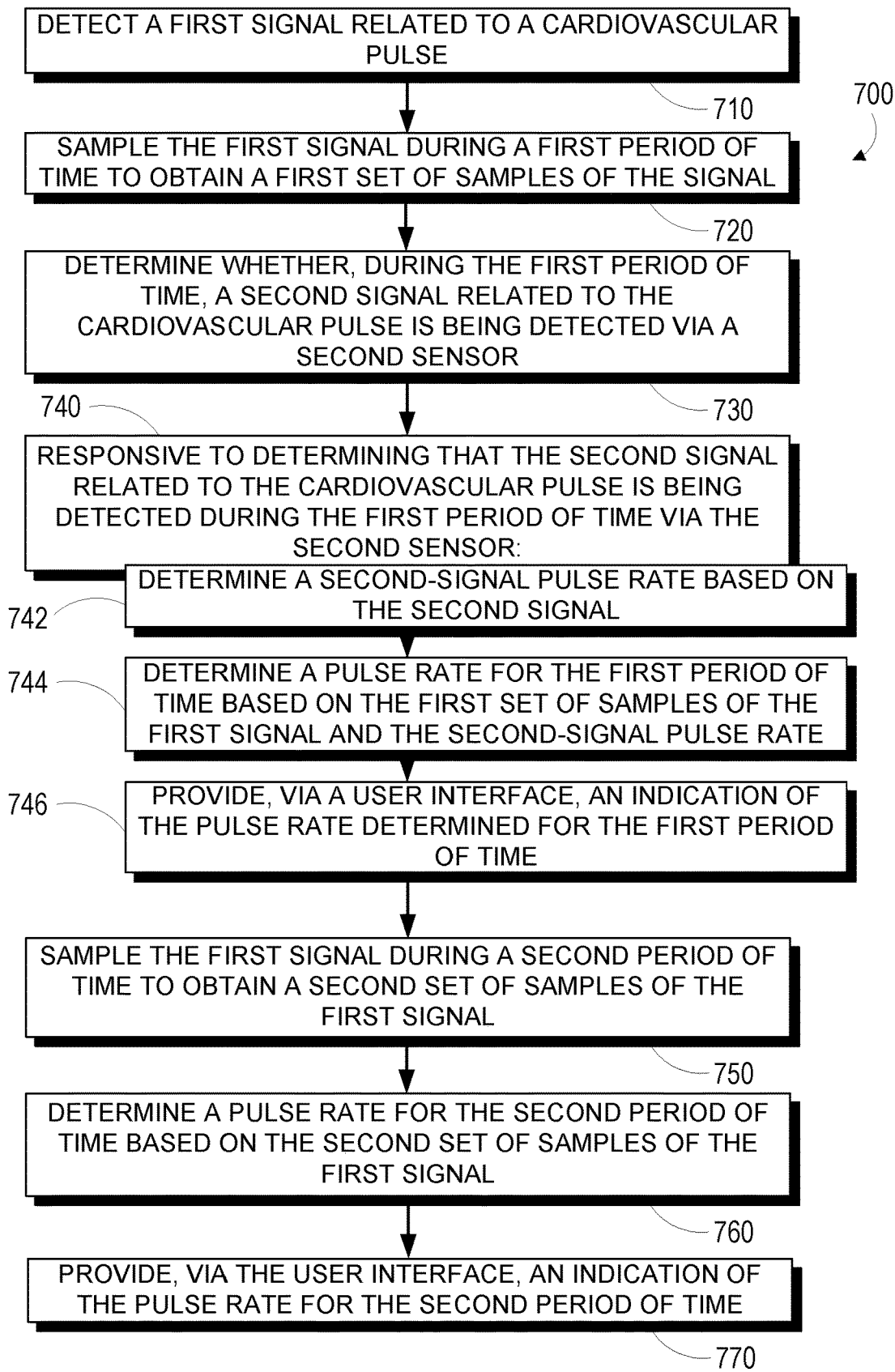
FIG. 7 is a flow chart of an example method.

FIG. 7 is a flowchart of a method 700 for determining cardiovascular pulse rates based on one or more detected signals related to the cardiovascular pulse and providing indications related to such determined pulse rates. The method 700 includes detecting a first signal that is related to the cardiovascular pulse (710). This could include operating a sensor to detect an intensity of light, a pattern of constructive and destructive interference in received light, a pressure, a temperature, an acceleration, a displacement, a color, a flow rate, or some other property related to a cardiovascular pulse, e.g., using a pressure sensor, a light sensor, a light emitter, a tonometer, an ultrasonic transducer, or some other sensing means. In some examples, detecting a first signal (710) could include detecting a plethysmographic signal, i.e., a signal related to a volume of blood in a portion of subsurface vasculature. Detecting such a signal could include operating a light source to illuminate a portion of subsurface vasculature and operating a light sensor to detect an intensity or other property of light responsively scattered by, reflected by, or otherwise emitted from the portion of subsurface vasculature. The method 700 additionally includes sampling the first signal during a first period of time to obtain a first set of samples of the first signal (720). This could include operating an analog to digital converter (ADC) to sample the first signal at a plurality of points in time during the first period of time.

The method 700 additionally includes determining whether, during the first period of time, a second signal related to the cardiovascular pulse is being detected via a second sensor (730). This could include obtaining a set of samples the second signal during the first period of time and performing some operations on the set of samples to determine whether the second signal is related to the cardiovascular pulse during the first period of time. For example, a quality or timing of features (e.g., QRS complexes, peaks, triangular waveforms of a photoplethysmographic signal) of the signal, a signal-to-noise ratio of the signal, a power of the signal in one or more frequency bands, a power spectrum of the signal, a variability of a pulse rate determined from the signal, or some other parameters could be determined, using the output of the second sensor, to determine whether the second signal, detected by the second sensor, is related to the cardiovascular pulse during the first period of time. Determining whether, during the first period of time, a second signal related to the cardiovascular pulse is being detected via a second sensor (730) could additionally or alternatively include detecting some other physical variable related to the second sensor, e.g., detecting an impedance between electrodes of the second sensor (e.g., to determine whether both electrodes are in reliable electrical contact with skin of a person), detecting a force or pressure between the second sensor and a skin surface, or detecting some other signal related to whether the second signal is related, during the first period of time, to the cardiovascular pulse.

The method 700 additionally includes, responsive to determining that the second signal related to the cardiovascular pulse is being detected during the first period of time via the second sensor, preforming a number of steps (740). The steps performed responsive to determining the second signal is being detected (740) include determining a second-signal pulse rate based on the second signal (742). This could include determining a spectral content of the second signal (e.g., determining a power spectrum, determining a spectrogram, applying a number of bandpass filters) and using the determined spectral content to determine the second-signal pulse rate (e.g., by determining a frequency of a peak or other feature of the determined spectral content). Determining a second-signal pulse rate based on the second signal (742) could include applying the second signal to one or more phase-locked loops or using some other method to determine the frequency of repeating patterns in the second signal. Determining a second-signal pulse rate based on the second signal (742) could include determining the timing, rate, period, or other information about features of the second signal during the first period of time (e.g., QRS complexes of an electrocardiographic signal, peaks of a signal).

The steps performed responsive to determining the second signal is being detected (740) further include determining a pulse rate for the first period of time based on the first set of samples of the first signal and the second-signal pulse rate (744). This could include determining a first-signal pulse rate based on the first set of samples of the first signal and combining (e.g., by a linear combination) the first-signal pulse rate and the second-signal pulse rate. Determining a pulse rate for the first period of time (744) could include determining, based on the first set of samples of the first signal, a number of potential pulse rates (e.g., based on the frequencies of peaks of spectral content determined from the first set of samples) and selecting one of the potential pulse rates based on the second-signal pulse rate (e.g., based on differences between the second-signal pulse rate and the potential pulse rates). Determining a pulse rate for the first period of time (744) could include setting the pulse rate for the first period of time equal to the determined second-signal pulse rate. A pulse rate for the first period of time could be determined by some other method The steps performed responsive to determining the second signal is being detected (740) further include providing, via a user interface, an indication of the pulse rate determined for the first period of time (746). This could include operating a display (e.g., of a wrist-mounted device that includes one or both of the first and second sensors) to provide a visual indication of the determined pulse rate. The visual indication could include a numerical indication (e.g., a frequency of the pulse rate in Hertz, a number of beats per minute), a qualitative indication (e.g., 'high', 'normal', 'low', 'elevated'), or some other visual indication. Additionally or alternatively, an audio indication (e.g., a voice reciting the pulse rate, a tone or other sound having a frequency, timbre, or other properties corresponding the pulse rate), a tactile indication (e.g., a vibration delivered to skin of a person that has a timing, duration, intensity, or other properties corresponding to the pulse rate), or some other indication may be provided of the pulse rate determined for the first period of time.

The method 700 additionally includes sampling the first signal during a second period of time to obtain a second set of samples of the first signal (750). The second period of time could be after the first period of time. In such examples, the method 700 could be performed causally; that is, a pulse rate of the cardiovascular pulse that is determined for any particular period of time could be determined based on signals detected during or prior to the particular point in time. Alternatively, the second period of time could be before the first period of time. As noted above, sampling the first signal could include operating an analog to digital converter (ADC) to sample the first signal; for step 750, the signal could be sampled at a plurality of points in time during the second period of time.

The method 700 additionally includes determining a pulse rate for the second period of time based on the second set of samples of the first signal (760). The pulse rate for the second period of time could be determined based on samples of the first signal as the second signal may not be available for determining a pulse rate during the second period of time. For example, the second signal, during the second period of time, could exhibit noise or other signal content that precludes use of the second signal, during the second period of time, to determine a pulse rate. In some examples, the second sensor could not be in contact with a target tissue during the second period of time, electrodes of the second sensor could be not in contact with appropriate skin locations during the second period of time, or some other circumstance related to the second sensor could prevail during the second period of time to prevent use of the second signal, detected using the second sensor during the second period of time, to determine a pulse rate for the second period of time.

Determining a pulse rate for the second period of time (760) could include operating one or more phase-locked loops (e.g., a hardware phase-locked loop, a phase-locked loop implemented digitally by a controller) to lock in to a repeating pattern(s) in the second set of samples, determining spectral content (e.g., a spectrogram, a power spectrum) and determining the pulse rate based on properties of the determined spectral content (e.g., frequencies of peaks or other features of the spectral content), or performing some other determinations based on the second set of samples. The pulse rate for the second period of time could also be determined based on pulse rates determined for other periods of time, e.g., based on a pulse rate determined for the first period of time, and/or on other information related to other periods of time. This could include determining the pulse rate for the second period of time by using the Viterbi algorithm, an inertial filter, the alpha-beta filter, a hidden Markov model, or some other methods to determine a pulse rate for the second period of time as part of a determined sequence of pulse rates for a plurality of different periods of time. Such a sequence could be constrained by the pulse rate determined for the first period of time, e.g., the pulse rate determined for the first period of time could be used as a seed value or starting value for the determination of pulse rates for periods of time subsequent and/or prior to the first period of time (e.g., for the second period of time). Other methods could be used to determine a pulse rate for the second period of time based on the second set of samples of the first signal (760).

The method 700 additionally includes providing, via the user interface, an indication of the pulse rate determined for the second period of time (770). As noted above, such an indication could include a visual indication, an auditory indication, a tactile indication, or any other sort of indication. Further, such an indication could be provided by a user interface of a device that includes one or both of the first and second sensors, or could be provided by a further device that is in direct or indirect communication with one or more devices that include the first and second sensors.

The method 700 could include additional steps or elements in addition to those illustrated in FIG. 7. For example, the method 700 could include detecting an artifact signal and using the artifact signal to remove unwanted content (e.g., noise content, motion artifact content) of signals detected using the first and/or second sensor. The method 700 could include determining a plurality of pulse rates, for a plurality of periods of time, and could further include filtering such pulse rates (e.g., using a bidirectional statistical filter). Additional and/or alternative steps of the method 700 are anticipated.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, pulse rates, health states, or other information about the user, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect cardiovascular pulse rates of a human body, it is noted that the disclosed devices, systems, and methods can be applied in other contexts as well. For example, detection systems configured to determine pulse rates or other frequency information related to oscillating patterns in biosignals or other detected signals may be included in wearable (e.g., body-mountable) and/or implantable devices. In some contexts, such a detection system is situated to be substantially encapsulated by bio-compatible polymeric material suitable for being in contact with bodily fluids and/or for being implanted.

In other examples, devices, systems, and methods disclosed herein may be applied to determine pulse rates or other frequency information related to oscillating patterns in biosignals or other signals detected form or in environments that are not in or on a human body. For example, detection systems disclosed herein may be included in devices used to measure cardiovascular pulse rates of an animal.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A method comprising:
during a first period of time, detecting a first-sensor signal from a first sensor;
determining a pulse rate for the first period of time based on the first-sensor signal detected during the first period of time;
during a second period of time, detecting the first-sensor signal from the first sensor and a second-sensor signal from a second sensor, wherein the second period of time is after the first period of time;
determining a pulse rate for the second period of time based on the first-sensor signal detected during the second period of time and the second-sensor signal detected during the second period of time;

updating the pulse rate for the first period of time based on the determined pulse rate for the second period of time; and providing, via a user interface, an indication of the updated pulse rate for the first period of time.

2. The method of claim 1, wherein determining the pulse rate for the first period of time based on the first-sensor signal detected during the first period of time comprises:

sampling the first-sensor signal during the first period of time to obtain a first set of samples of the first-sensor signal; and determining the pulse rate for the first period of time based on the first set of samples of the first-sensor signal.

3. The method of claim 2, wherein determining the pulse rate for the second period of time based on the first-sensor signal detected during the second period of time and the second-sensor signal detected during the second period of time comprises:

sampling the first-sensor signal during the second period of time to obtain a second set of samples of the first-sensor signal;

determining a second-signal pulse rate based on the second-sensor signal detected during the second period of time; and determining the pulse rate for the second period of time based on (i) the second set of samples of the first-sensor signal and (ii) the second-signal pulse rate.

4. The method of claim 3, wherein determining the pulse rate for the second period of time based on (i) the second set of samples of the first-sensor signal and (ii) the second-signal pulse rate comprises:

determining a plurality of potential pulse rates based on the second set of samples of the first-sensor signal; and selecting one of the potential pulse rates as the pulse rate for the second period of time.

5. The method of claim 4, wherein selecting one of the potential pulse rates as the pulse rate for the second period of time comprises:

for each potential pulse rate, determining a respective difference between the potential pulse rate and the second-signal pulse rate; and selecting the potential pulse rate that has the smallest difference as the pulse rate for the second period of time.

6. The method of claim 3, wherein determining the pulse rate for the second period of time based on (i) the second set of samples of the first-sensor signal and (ii) the second-signal pulse rate comprises:

determining a spectral content of the first-sensor signal during the second period of time based on the second set of samples of the first signal; and determining the pulse rate for the second period of time based on the determined spectral content and the second-signal pulse rate.

7. The method of claim 1, wherein the first-sensor signal is a photoplethysmographic signal.

8. The method of claim 1, wherein the second-sensor signal is an electrocardiographic signal.

9. The method of claim 1, further comprising:

sampling the second-sensor signal during the second period of time to obtain a set of samples of the second-sensor signal; and determining whether a reliable pulse rate can be determined from the set of samples of the second-sensor signal.

10. The method of claim 9, wherein determining the pulse rate for the second period of time based on the first-sensor signal detected during the second period of time and the second-sensor signal detected during the second period of time is responsive to a determination that a reliable pulse rate can be determined from the set of samples of the second-sensor signal.

11. A system comprising:

a first sensor;

a second sensor;

a user interface; and a controller operably coupled to the first sensor and the second sensor, wherein the controller comprises a computing device programmed to perform controller operations comprising:

during a first period of time, detecting a first-sensor signal from the first sensor;

determining a pulse rate for the first period of time based on the first-sensor signal detected during the first period of time;

during a second period of time, detecting the first-sensor signal from the first sensor and a second-sensor signal from the second sensor, wherein the second period of time is after the first period of time;

determining a pulse rate for the second period of time based on the first-sensor signal detected during the second period of time and the second-sensor signal detected during the second period of time;

updating the pulse rate for the first period of time based on the determined pulse rate for the second period of time; and providing, via the user interface, an indication of the updated pulse rate for the first period of time.

12. The system of claim 11, wherein determining the pulse rate for the first period of time based on the first-sensor signal detected during the first period of time comprises:

sampling the first-sensor signal during the first period of time to obtain a first set of samples of the first-sensor signal; and determining the pulse rate for the first period of time based on the first set of samples of the first-sensor signal.

13. The system of claim 12, wherein determining the pulse rate for the second period of time based on the first-sensor signal detected during the second period of time and the second-sensor signal detected during the second period of time comprises:

sampling the first-sensor signal during the second period of time to obtain a second set of samples of the first-sensor signal;

determining a second-signal pulse rate based on the second-sensor signal detected during the second period of time; and determining the pulse rate for the second period of time based on (i) the second set of samples of the first-sensor signal and (ii) the second-signal pulse rate.

14. The system of claim 13, wherein determining the pulse rate for the second period of time based on (i) the second set of samples of the first-sensor signal and (ii) the second-signal pulse rate comprises:

determining a plurality of potential pulse rates based on the second set of samples of the first-sensor signal; and selecting one of the potential pulse rates as the pulse rate for the second period of time.

15. The system of claim 14, wherein selecting one of the potential pulse rates as the pulse rate for the second period of time comprises:

for each potential pulse rate, determining a respective difference between the potential pulse rate and the second-signal pulse rate; and selecting the potential pulse rate that has the smallest difference as the pulse rate for the second period of time.

16. The system of claim 13, wherein determining the pulse rate for the second period of time based on (i) the second set of samples of the first-sensor signal and (ii) the second-signal pulse rate comprises:

determining a spectral content of the first-sensor signal during the second period of time based on the second set of samples of the first signal; and determining the pulse rate for the second period of time based on the determined spectral content and the second-signal pulse rate.

17. The system of claim 11, wherein the first sensor is a photoplethysmographic sensor.

18. The system of claim 11, wherein the second sensor is an electrocardiographic sensor.

19. The system of claim 11, wherein the controller operations further comprise:

sampling the second-sensor signal during the second period of time to obtain a set of samples of the second-sensor signal; and determining whether a reliable pulse rate can be determined from the set of samples of the second-sensor signal.

20. The system of claim 19, wherein determining the pulse rate for the second period of time based on the first-sensor signal detected during the second period of time and the second-sensor signal detected during the second period of time is responsive to a determination that a reliable pulse rate can be determined from the set of samples of the second-sensor signal.

* * * * *